United States Patent [19]

Schwarz

[11] 4,071,516
[45] Jan. 31, 1978

[54] 4-(ACYLOXYPHENYL)-QUINAZOLIN-2(1H)-ONES

[75] Inventor: Hans J. Schwarz, Parsippany, N.J.

[73] Assignee: Sandoz, Inc., E. Hanover, N.J.

[21] Appl. No.: 716,138

[22] Filed: Aug. 20, 1976

[51] Int. Cl.² .............. C07D 239/82; C07D 295/06; C07D 295/10; A61K 31/505

[52] U.S. Cl. .............. 260/251 QB; 424/248.54; 424/251; 424/248.55; 544/116; 544/119; 542/427; 542/405

[58] Field of Search ........ 260/251 QB, 240 A, 240 K, 260/247.2 A

[56] References Cited

U.S. PATENT DOCUMENTS 3,723,432  3/1973  Ott .................................. 260/251 QB

FOREIGN PATENT DOCUMENTS

| 802,662 | 1973 | Belgium. |
| 769,858 | 1971 | Belgium. |
| 788,213 | 1973 | Belgium. |
| 7,213,273 | 1972 | Japan. |
| 1,008,287 | 1974 | Japan. |
| 1,181,570 | 1970 | United Kingdom. |

Primary Examiner—Raymond V. Rush
Attorney, Agent, or Firm—Gerald D. Sharkin; Richard E. Vila

[57] ABSTRACT

Anti-inflammatories and analgesics of the formula:

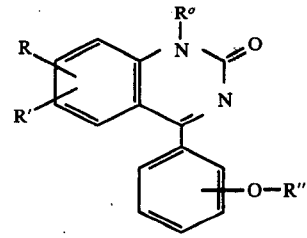

wherein R° is alkyl, R is hydrogen, alkyl, halo, nitro or R'''OOC—, R' is hydrogen, alkyl or halo, R'' is a hydrolyzable carboxylic acid acyl group and R''' is hydrogen or alkyl.

22 Claims, No Drawings

4-(ACYLOXYPHENYL)-QUINAZOLIN-2(1H)-ONES

This invention relates to 4-phenyl-1-substituted-quinazolin-2(1H)-ones in which the 4-phenyl group is substituted by a hydrolyzable carboxylic acid acyloxy group, and to methods of preparing the same. The invention also relates to pharmaceutical compositions and methods for utilization of the pharmacological properties of said quinazolinones.

The quinazolin-2(1H)-ones of the invention may be represented by the formula I:

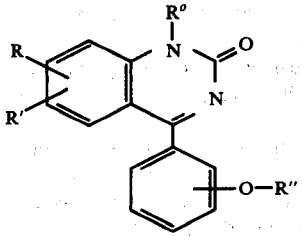

I wherein
  $R^o$ is alkyl of 1 to 6 carbon atoms,
  R is hydrogen, fluoro, chloro, bromo, alkyl of 1 to 4 carbon atoms, nitro or —COOR''',
  R' is hydrogen, fluoro, chloro, bromo or alkyl of 1 to 4 carbon atoms,
  R'' is a carboxylic acid acyl group blood-hydrolyzable to a hydroxy group and
  R''' is hydrogen or alkyl of 1 to 4 carbon atoms, with the proviso that R' is hydrogen or halo when R is —COOR'''.

The terms "hydrolyzable carboxylic acid acyl group" and the like as used herein means a conventional ester derivative of the phenol group bearing compound of the formula II:

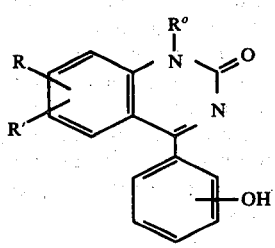

II wherein $R^o$, R and R' are as above defined, and hydrolyzable in blood to said compound of the formula II. The terms "carboxylic acid", "carboxylic acid acyl" and the like as used herein are meant to designate not only compounds or residues of compounds which can be isolated in a form including a carboxy function, i.e. —COOH, but compounds capable of possessing or forming an acyloxy ester residue. The definition of R'' includes, without limitation, acetyl, propionyl, caproyl, benzoyl, toluyl, phenylacetyl, β-phenylpropionyl, cinnamoyl, aminoacetyl, morpholinoacetyl, chloroacetyl, chlorobenzoyl and bromo benzoyl. In general, the carboxylic acid acyl group (R'') is desirably the carboxylic acid acyl group of a non-toxic and otherwise pharmacologically acceptable carboxylic acid.

The terms "blood-hydrolyzable" and the like shall be taken, for definition purposes, as referring to an arbitrary and convenient standard test in which at least 50 mol percent of the drug candidate is hydrolyzed in no more than 12 hours at a concentration of 2.5 milligrams of the drug candidate in 100 ml. of freshly drawn rat blood at 37° C. The percentage hydrolyzed may be determined by standard assay techniques including chromatography, e.g. thin layer chromatography. If desired, the 2-position carbon atom of the quinazolinone may be radioactively tagged (carbon$_{14}$) to facilitate analysis. While the standard test indicated herein is conveniently carried out using the blood of the rat, it will be evident to those skilled in the art that the desired hydrolysis is effected by the blood esterases and that substantially similar results would be expected in the blood of essentially any mammal that would be a proposed host for the drug.

The compounds of the formula I may be prepared from the compounds of the formula II by any of several acylating procedures well known to those skilled in the art. For example, the compound of the formula II may be subjected to conventional acylating reactions with carboxylic acids, carboxylic acid anhydrides or carboxylic acid halides. Other compounds of the formula I may be prepared from the products resulting from the acylating of a compound II. For example, a compound I in which R'' is a haloacyl, e.g. chloroacetyl, may be reacted with an amine, e.g. morpholine to form aminoacyl esters, e.g. compounds I in which R'' is morpholinoacetyl. The particular reaction procedure selected will usually depend on known factors such as ease of reaction, sources of starting materials and the like. In general, the known acylation reactions may be effected at temperatures in the range of from 0° C. to 180° C.

The above-referred to conventional acylating procedures as applied to the preparation of the final products of the formula I may be represented as involving the reaction of a compound of the formula II with a compound of the formula III:

$(R'')_{2-n}A$  III wherein R'' is as above defined, n is 0 or 1 and A is oxygen or halo of atomic weight of from 35 to 80, i.e. chloro or bromo, with the proviso that n is 0 when A is oxygen and n is 1 where A is halo. When A is oxygen (and n is 0) the reaction is preferably carried out in the absence of added solvent employing an excess of the carboxylic acid anhydride as essentially the sole reaction medium. Such reaction may be conveniently effected at elevated temperatures of the order of from 60° C to 180° C., preferably 80° C. to 120° C., in a reaction mixture consisting essentially of the compound II and compound IIIa, i.e. a compound of the formula:

$(R'')_2O$  IIIa

However, when employing temperatures not above about 60° C, particularly from 0° C. to 50° C, preferably, 15° C. to 40° C, it generally preferred to also employ a dehydrating agent of known suitability for such reactions, for example, concentrated sulfuric acid. In some cases an alkali metal carboxylate, e.g. sodium acetate, may be employed essentially as a buffering agent. When n is 1 and A is halo, the reaction of the resulting compound IIIb:

R''—X  IIIb IIIb wherein R'' is as above defined and X is chloro or bromo, preferably chloro, is carried out in an aqueous medium in the presence of a water soluble base which may be either of the organic or inorganic type, e.g. pyridine or an alkali metal carbonate such as sodium carbonate. The reaction of a compound II with a compound IIIb may be effected at temperatures of from 0° C. to 60° C., preferably 15° C. to 40° C.

In general, the reaction product of the formula I may be isolated and recovered from the reaction mixture in which it is formed by working up by established procedures.

The compounds of the formula II in which R is other than —COOR''', and their preparation, are disclosed in the literature, for example, in U.S. Pat No. 3,723,432, and essentially involves hydrolysis of the corresponding alkoxyphenyl substituted quinazolinone, e.g. by treatment with aqueous hydrobromic acid.

The compounds of the formula II in which R is —COOR''' and R''' is hydrogen may be prepared by oxidizing a compound of the formula IIA:

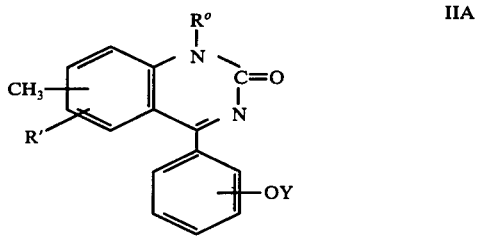

wherein $R^o$ and R' are as defined and Y is hydrogen or alkyl of 1 to 4 carbon atoms, and hydrolysing the resulting product when Y is alkyl.

The preparation of compounds II in which R is —COOH from compounds IIA may be conveniently carried out in an aqueous solution at temperatures of from 20° C. to 150° C., preferably 60° C. to 120° C., employing oxidizing agents such as potassium permanganate, manganese dioxide and the like, preferably potassium permanganate. The reaction is preferably carried out in the presence of an inorganic base, e.g. sodium carbonate. It is generally preferred to employ a compound IIA in which Y is alkyl and hydrolyse the resulting product.

The compounds of the formula II in which R is —COOR''' and R''' is alkyl may be prepared by esterification of a compound of the formula IIB:

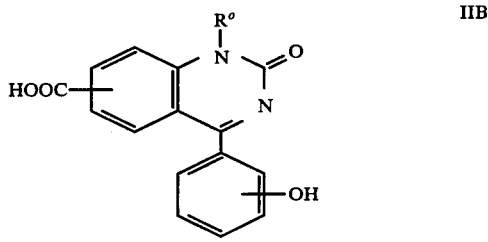

wherein $R^o$ is as above defined.

The esterification of a compound IIB may be carried out at temperatues in the range of from 30° C. to 80° C. under anhydrous conditions and in the presence of hydrogen chloride and an excess of the alkanol corresponding to the R''' alkyl group, such excess also serving as solvent for the reaction.

The compounds of the formula IIA and their preparation are also described in the literature, e.g. in U.S. Pat. No. 3,723,432.

The compounds of structural formula I are useful because they possess pharmacological activity in animals. In particular, the compounds are useful as anti-inflammatory agents as indicated by Carrageenan-induced edema tests on rats (oral and i.v. administration), wherein:

(a) the difference in foot volume is measured by difference in mercury displacement (the drug effect being measured 3 hours after carrageenan); and b) the swelling of the paw edema and drug effect are measured by an Antiphlogmeter according to Hemper and Ameln, Zeitschr. Ges. Exp. Med. 131, 407 (1959), by determining the change in capacity in a condenser, (the drug effect being the average of readings taken 3 and 5 hours after carrageenan). The compounds of the invention are of interest by reason of exhibiting their activity more significantly in the latter method (b) of evaluation than the former.

For such use, the compounds may be combined with a pharmaceutically acceptable carrier, and such other conventional adjuvants as may be necessary, and administered orally in such forms as tablets, capsules, elixirs, suspensions and the like or parenterally in the form of an injectable solution or suspension. The dosage administered will, of course, vary depending upon the compounds used and the mode of administration. However, in general, satisfactory results are obtained when administered at a daily dosage of from about 1.5 milligrams to about 200 milligrams per kilogram of body weight, preferably given in divided doses 2 to 4 times a day, or in sustained release form. For most mammals the administration of from about 100 milligrams to about 2000 milligrams of the compound per day provides satisfactory results and dosage forms suitable for internal administration comprise from about 25 milligrams to about 1000 milligrams of the compound in admixture with a solid or liquid pharmaceutical carrier or diluent.

The compounds I of the invention are also useful as analgesics as indicated by application of pressure to yeast-inflamed foot of the rat (oral administration). For such use, the compound may be administered to obtain satisfactory results at dosages and in modes similar to those employed in the treatment of inflammation.

A representative formulation is a capsule prepared by conventional techniques for administration 2 to 4 times a day for treatment of inflammation and containing the following ingredients:

| Ingredient | Parts by Weight |
|---|---|
| 7-methyl-1-isopropyl-4-(m-acetoxyphenyl)-2(1H)-quinazolinone | 75 |
| Lactose | 225 |

The generally preferred compounds of the formula I have one or more of the following characteristics:
(a) $R^o$ being a branched alkyl; (b) R being hydrogen, fluoro, chloro, bromo or alkyl of 1 or 2 carbon atoms; (c) R' being hydrogen or alkyl of 1 or 2 carbon atoms; and (d) the —OOCR'' moiety being in the m- or p-position of the 4-phenyl ring; and (e) R'' being alkanoyl of 2 to 20 total carbon atoms or optionally mono-substituted benzoyl in which said optional substituents are fluoro, chloro, bromo or alkyl of 1 to 4 carbon atoms located at the meta- or para-positions. Within the above indicated preferences are the following more desired preferences: (a) $R^o$ being isopropyl; (b) R being methyl or ethyl at the 7-position; (c) R' being hydrogen; (d) the —OOCR'' moiety being in the m-position of the 4-phenyl ring; and (e) R" being alkanoyl of 2 to 6 carbon atoms particularly acetyl. The particularly preferred compounds have two or more of the above indicated general preferences and desired preferences in combination, and the especially preferred compounds have all such general preferences in combination and the still further especially preferred compounds have all the desired preferences in combination.

The following examples show representative compounds emcompassed within the scope of this invention and the manner in which such compounds are prepared. However, it is to be understood that the examples are for purposes of illustration only.

EXAMPLE 1

1-Isopropyl-4-(3-acetoxyphenyl)-7-methyl-2(1H)-quinazolinone

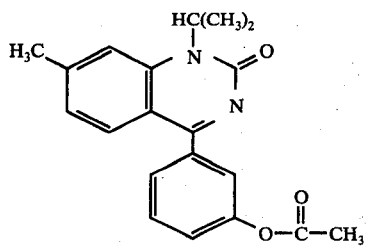

Step A, 3,4-Dihydro-1-isopropyl-4-(3-methoxyphenyl)-7-methyl-2(1H)-quinazolinone

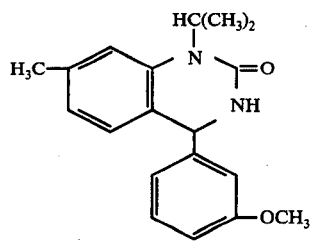

To a vessel equipped with agitation means, thermometer and a reflux condenser is added 6.40 g of N-isopropyl, N-(m-tolyl) urea, 22.21 g of m-methoxy benzaldehyde, and 255 ml of toluene. The temperature of the mixture is slowly raised (about 25 min.) to 110° C to start refluxing. After refluxing for 5 min. the temperature is lowered to 100° C and 0.12 g (0.082 ml) of methanesulphonic acid is added. The temperature is again increased to 110° C and refluxing maintained for 3 hours. The reaction mixture is then allowed to cool to room temperature, washed 4 times with dilute sulfuric acid (20% w/v) resulting in the formation of a brown-orange gummy material (undesirable material). The organic phase is then washed 4 times with 25 ml portion of water (pH of last wash 5), then dried over anh. soidum sulfate and evaporated (steam distilled) to obtain a residue. The residue is taken up in benzene, and chromatographed on a silica column; starting with benzene then increasing proportions of chloroform (20%, 50%, then 100% chloroform). The samples obtained from 100% chloroform are combined, evaporated to dryness, then crystallized from chloroform to obtain 3,4-dihydro-1-isopropyl-4-(3--methoxyphenyl)-7-methyl-2(1H)-Quinazolinone, mp 167-169.

Step B, 1-Isopropyl-4-(3-methoxyphenyl)-7-methyl-2(1H)-quinazolinone

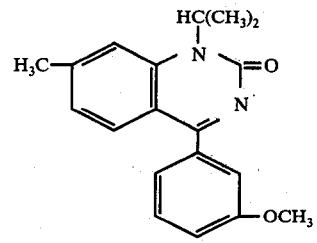

1.555 g of 3,4-dihydro-1-isopropyl-4-(3-methoxyphenyl)-7-methyl-2(1H)-quinazolinone in 40 ml of p-dioxane is charged to a vessel having a dropping funnel, agitation means and thermometer. The charged vessel is cooled in a water bath (running water at 14°); a slution of 0.88 g of potassium permanganate in 20 ml of water is placed in the dropping funnel, which is then added dropwise to the vessel with stirring during which temperatures range from 15° to 18°). The reaction mixture is then allowed to rise to room temperature (26°), at which is stirred for 2 hr. 20 min. 0.38 ml of aqueous formaldehyde (37%) is then added, and the mixture stirred for 10 minutes. The mixture is then filtered through celite (diatomaceous earth), and the filtrate retained. The filter cake is then washed with 75 ml of water/p-dioxane (20:15), the washings and filtrate are combined, extracted four times with 20 ml portions methylenechloride. The combined extracts are then evaporated to dryness to obtain a residue which is taken up in 100 ml benzene, 100 ml of petroleum ether added thereto, the solution filtered through 0.5 g of charcoal, (at room temperature) and then evaporated to dryness to obtain 1-isopropyl-4-(3-methoxyphenyl)-7-methyl-2(1H)-quinazolinone.

Step C, 1-Isopropyl-4-(3-hydroxyphenyl)-7-methyl-2(1H)-quinazolinone.

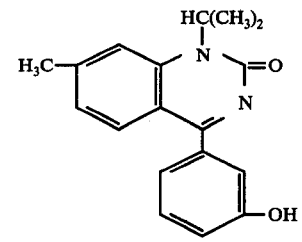

To 0.5 g of 1-isopropyl-4-(3-methoxyphenyl)-7-methyl-2(1H)-quinazolinone is added 5 ml of 48% (aqueous) hydrobromic acid (heat evolves and the solution turns yellow). The mixture is then refluxed for 6 hours. The mixture is cooled to room temperature, then 95 ml of water added, and the resulting mixture extracted thrice with 100 ml portions of a benzene: n-butanol (4:1) mixture each extract is retained separately. Each extract is washed 4 times with 75 ml portions of water (the pH of the last wash should be neutral). The extracts are combined and evaporated to dryness to obtain a residue which is then crystallized from methanol and ethyl acetate (1:1) to obtain 1-isopropyl-4-(3-hydroxyphenyl)-7-methyl-2(1H)-quinazolinone; m.p. 270°–272°, which yields refined product upon recrystallization from methanol; m.p. 274°–275° C.

Step D, 1-isopropyl-4-(3-acetoxyphenyl)-7-methyl-2(1H)-quinazolinone

To 5.0 g of refined 1-isopropyl-4-(3-hydroxyphenyl)-7-methyl-2(1H)-quinazolinone in a vessel, is added 100 ml of acetic anhydride and 0.5 ml. of concentrated sulfuric acid. The resulting mixture is allowed to stand for 16 hours. The reaction mixture is then poured over salted ice in a vessel. After the ice has melted, the resulting liquid is extracted twice with 300 ml portions of benzene: n-butanol (4:1) and the combined extracts washed with distilled water until free of acid, and then evaporated to obtain a residue. The residue is crystallized from methanol to obtain the title product, m.p. 148°–150°.

EXAMPLE 2

Following the procedure of Example 1 the following compounds are prepared:
- A. 1-isopropyl-4-(p-acetoxyphenyl)-7-methyl-2(1H)-quinazolinone.
- B. 1-isopropyl-7-chloro-4-(m-acetoxyphenyl)-2(1H)-quinazolinone.
- C. 1-isopropyl-5,7-dimethyl-4-(m-acetoxyphenyl)-2(1H)-quinazolinone.
- D. 1-tert. butyl-6-nitro-4-(m-acetoxyphenyl)-2(1H)-quinazolinone (following Steps C and D of Example 1 only; with the m-methoxyphenoxy intermediate prepared analogously to Example 48 of U.S. Pat No. 3,723,432).
- E. 1-isopropyl-4-(o-acetoxyphenyl)-7-methyl-2(1H)-quinazolinone.
- F. 1-isopropyl-4-(m-benzoyloxyphenyl)-7-methyl-2(1H)-quinazolinone.

EXAMPLE A

7-Carboxy-1-isopropyl-4-(m-methoxyphenyl)-2(1H)-quinazolinone.

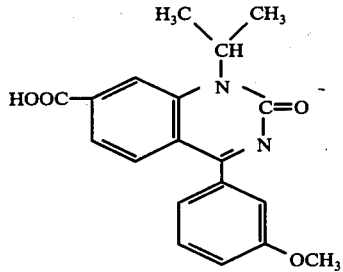

A mixture of 11.25 g. of 1-isopropyl-7-methyl-4-(m-methoxyphenyl)-2(1H)-quinazolinone, 5.25 g. of sodium carbonate and 750 ml. of water is refluxed with 7.5 g. of potassium permanganate being added every half hour until a total of 52.5 g. of potassium permanganate is added. After refluxing for an additional 45 minutes, the reaction mixture is cooled, acidified on the slow addition of 263 ml. of 6N. hydrochloric acid and then treated with sodium sulfate until the manganese dioxide is eliminated. The resulting mixture is cooled and filtered to recover the precipitate which is washed with water, dried under vacuum (40° C.) and crystallized from hot glacial acidic acid to obtain 7-carboxy-1-isopropyl-4-(m-methoxyphenyl)-2(1H)-quinazolinone.

EXAMPLE B

7-Carbomethoxy-1-isopropyl-4-(m-methoxyphenyl)-2(1H)-quinazolinone.

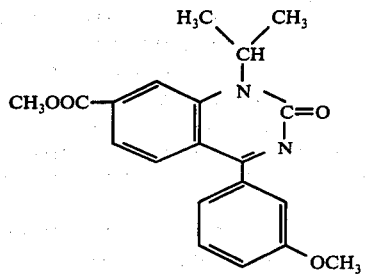

Into a flask containing 7.0 g. of 7-carboxy-1-isopropyl-4-(m-methoxyphenyl)-2(1H)-quinazolinone dissolved in anhydrous methanol is introduced hydrogen chloride gas until the temperature reaches 50° C. The flask is then equipped with a stopper and the reaction mixture allowed to stand under ambient conditions for 7 hours. The resulting mixture is evaporated to dryness, the residue taken up in benzene, washed with water, followed by evaporation to dryness and crystallization of the residue from methanol to obtain 7-carbomethoxy-1-isopropyl-4-(m-methoxyphenyl)-2(1H)-quinazolinone, m.p. 164°–167° C.

EXAMPLE C

7-Carboxy-1-isopropyl-4-(m-hydroxyphenyl)-2(1H)-quinazolinone.

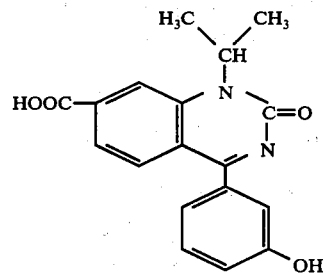

A mixture of 8.0 g. of 7-carboxy-1-isopropyl-4-(m-methoxyphenyl)-2(1H)-quinazolinone, 300 ml. of 48% hydrobromic acid and 210 ml. of glacial acidic acid is refluxed for 6 hours. The resulting solution is cooled to 10° C. and filtered to recover the precipitate which is washed with water and taken up in 250 ml. of glacial acidic acid. After refluxing for 2 hours, the reaction mixture is cooled to 20° C. and filtered to recover the precipitate which is washed with water and dried under vacuum (40° C.) to obtain 7-carboxy-1-isopropyl-4-(m-hydroxyphenyl)-2(1H)-quinazolinone, m.p. greater than 310° C.

EXAMPLE D

Following the procedure of Example B, the following compound is prepared from the product of Example C.
- A). 7-carbomethoxy-1-isopropyl-4-(m-hydroxyphenyl)-2(1H)-quinazolinone, m.p. 230°–232° C.

EXAMPLE 3

Following the procedure of Step D of Example 1 there is prepared:
- A. 7-carboxy-1-isopropyl-4-(m-acetoxyphenyl)-2(1H)-quinazolinone.

B. 7-carbomethoxy-1-isopropyl-4-(m-acetoxyphenyl)-2(1H)-quinazolinone.

The compounds of the formula I in which R''' is hydrogen may be converted to salt forms in which R''' is a cation. Such salt forms in which R''' is a pharmaceutically acceptable cation may be administered as pharmaceutical agents for the above-indicated usages in the same manner and at the same doses as indicated above for the other compounds of the formula I. Such pharmaceutically acception cations include, by way of illustration, the sodium, potassium and triethyl ammonium cation. In general, the salt forms may be produced from the corresponding acids, and vice-versa, by conventional procedures. An example of a preferred such salt is the sodium salt.

What is claimed is:

1. A compound of the formula

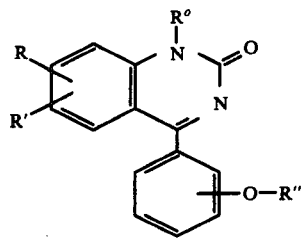

wherein
R° is alkyl of 1 to 6 carbon atoms,
R is hydrogen, fluoro, chloro, bromo, alkyl of 1 to 4 carbon atoms, nitro or —COOR''',
R' is hydrogen, fluoro, chloro, bromo or alkyl of 1 to 4 carbon atoms,
R'' is a carboxylic acid acyl group hydrolyzable in blood by esterases therein, and
R''' is hydrogen, alkyl of 1 to 4 carbon atoms or a pharmaceutically acceptable cation, with the proviso that R' is hydrogen or halo when R is —COOR'''.

2. A compound of claim 1 in which R'' is alkanoyl of 2 to 20 carbon atoms or benzoyl optionally monosubstituted in the meta- or para-position by fluoro, chloro, bromo or alkyl of 1 to 4 carbon atoms.

3. A compound of claim 2 in which R'' is alkanoyl of 2 to 6 carbon atoms.

4. A compound of claim 2 in which R° is branched alkyl.

5. A compound of claim 4 in which R is hydrogen, fluoro, chloro, bromo or alkyl and R' is hydrogen or alkyl.

6. A compound of claim 5 in which R° is isopropyl.

7. A compound of claim 6 in which R is 7-methyl or 7-ethyl.

8. A compound of claim 7 in which R' is hydrogen.

9. A compound of claim 1 which is 1-isopropyl-4-(o-acetoxyphenyl)-7-methyl-2(1H)-quinazolinone.

10. A compound of claim 1 in which the —OOCR'' moiety is at the meta or para position of the phenyl ring to which it is attached.

11. A compound of claim 10 in which R° is branched alkyl.

12. A compound of claim 11 in which R is hydrogen, fluoro, chloro, bromo or alkyl and R' is hydrogen or alkyl.

13. A compound of claim 12 in which R° is isopropyl.

14. A compound of claim 13 in which R is 7-methyl or 7-ethyl.

15. A compound of claim 14 in which the —OOCR'' moiety is at the meta-position.

16. The compound of claim 15 which is 1-isopropyl-7-methyl-4-(m-acetoxyphenyl)-2(1H)-quinazolinone.

17. The compound of claim 14 which is 1-isopropyl-7-methyl-4-(p-acetoxyphenyl)-2(1H)-quinazolinone.

18. A compound of claim 1 in which R is —COOR'''.

19. A compound of claim 18 in which R° is isopropyl and the —COOR''' is at the 7-position.

20. The compound of claim 19 which is 1-isopropyl-7-carboxy-4-(m-acetoxyphenyl)-2(1H)-quinazolinone.

21. The compound of claim 19 which is 1-isopropyl-7-carbomethoxy-4-(m-acetoxyphenyl)-2(1H)-quinazolinone.

22. The compound of claim 2 which is 1-isopropyl-4-(o-benzoyloxyphenyl)-7-methyl-2(1H)-quinazolinone.

* * * * *